Figure 1:
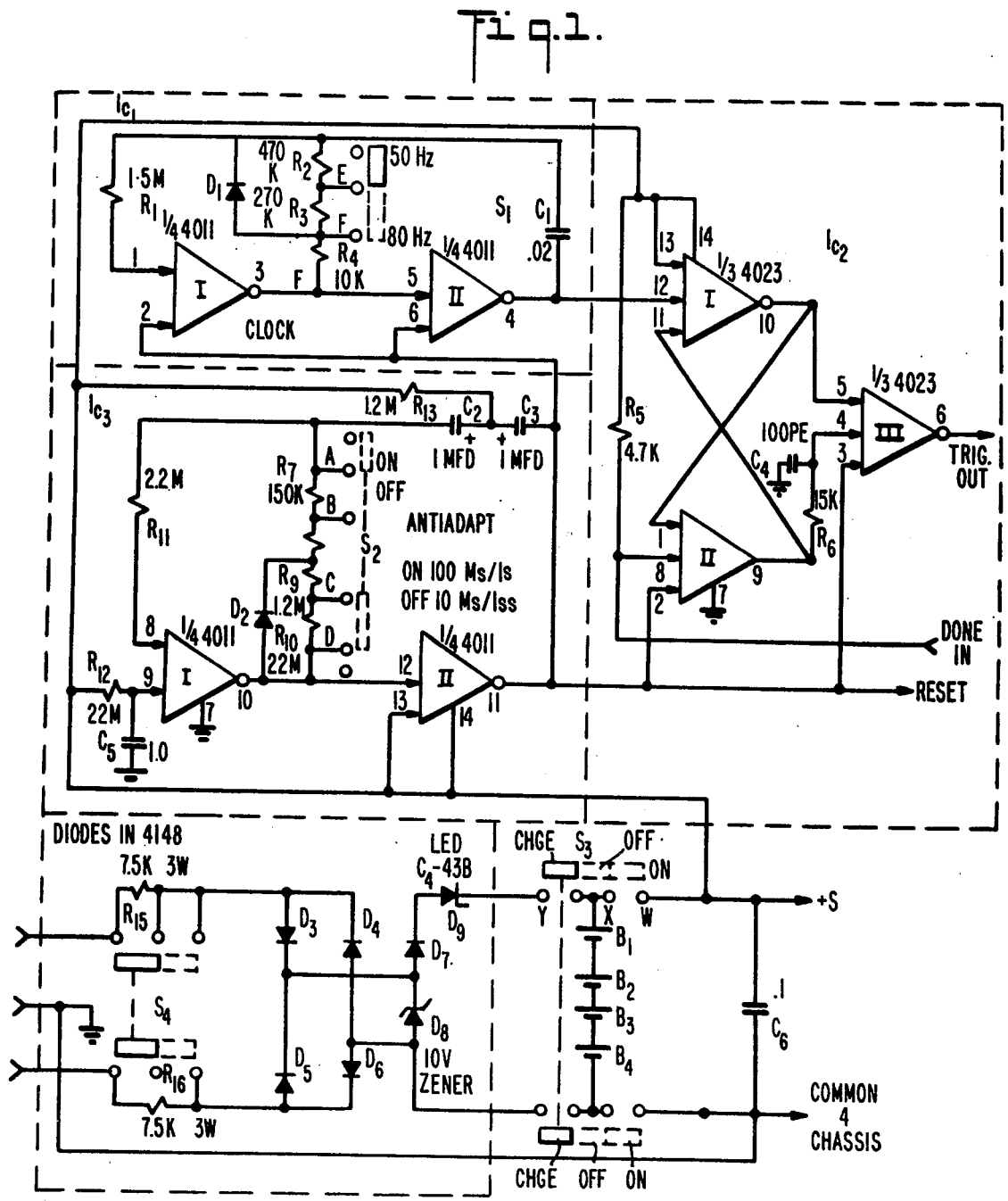

United States Patent [19]

Meretsky

[11] Patent Number: 4,482,856
[45] Date of Patent: Nov. 13, 1984

[54] BATTERY CHARGER

[75] Inventor: Paul L. Meretsky, Haifa, Israel

[73] Assignee: Technion Research and Development Foundation, Ltd., Haifa, Israel

[21] Appl. No.: 396,056

[22] Filed: Jul. 7, 1982

Related U.S. Application Data

[60] Continuation-in-part of Ser. No. 219,332, Dec. 17, 1980, abandoned, which is a division of Ser. No. 921,344, Jul. 3, 1978, Pat. No. 4,256,116.

[51] Int. Cl.³ ............................................. H02J 7/00
[52] U.S. Cl. ....................................... 320/59; 363/53; 363/126
[58] Field of Search ..................... 320/57, 59, DIG. 1; 363/126, 53

[56] References Cited

U.S. PATENT DOCUMENTS

| | | | |
|---|---|---|---|
| 3,123,759 | 3/1964 | Grey | 320/59 X |
| 3,327,198 | 6/1967 | Rauch | 320/DIG. 1 |
| 3,978,388 | 8/1976 | deVries | 363/53 X |
| 4,084,123 | 4/1978 | Lineback et al. | 320/2 |
| 4,155,081 | 5/1979 | Haglund | 320/48 X |

FOREIGN PATENT DOCUMENTS 1933082  1/1971  Fed. Rep. of Germany ........ 320/44

Primary Examiner—William M. Shoop
Attorney, Agent, or Firm—Browdy and Neimark

[57] ABSTRACT

The invention comprises a bridged, transformerless charger which will permit the use of inexpensive low power diodes and a battery saver which may be used to permit excess energy to charge batteries.

12 Claims, 1 Drawing Figure

BATTERY CHARGER

This application is a continuation-in-part of prior application Ser. No. 219,332, filed Dec. 17, 1980, now abandoned; which prior application was in turn a division of a still earlier prior application, Ser. No. 921,344, filed July 3, 1978, now issued as U.S. Pat. No. 4,256,116; both of said prior abandoned patent application and said issued patent being incorporated herein by reference as if here set forth in full.

The present invention relates to a transcutaneous pain reliever which relieves pain by the electrical stimulation of part of a patient's body, and more particularly to a battery charger useful in conjunction wich such a pain reliever as well as to charge batteries generally.

While the mechanics of suppressing pain by electrical impulses are not yet completely known, two theories appear to have to have been developed. In one theory, the electrical impulses arrive at the central nervous system faster than the pain impulses in order to modulate the pain impulses. This theory indicates that electrical impulses travel through the larger nerve fibres at greater speeds whereas pain impulses travel through smaller nerve fibres at slower rates.

A more recent theory which has been developed is the so-called "gate control" theory. According to that theory, pain relief is achieved because of the inhibition of certain nerve fibres by electrically activating the larger nerve fibres. There is a "gate" in the spinal cord which blocks pain signals from reaching the brain. This gate is closed by electrical stimulation of the larger nerve fibres so as to block pain signals to the brain coming through the smaller nerve fibres.

Regardless of the accuracy of either theory, various instruments using electric impulses to inhibit or suppress pain have been commercially available for many years. These existing instruments operate by exciting only a few electrodes attached to certain affected areas of the patient's body and are believed to be inadequate because of the limited areas stimulated. If larger numbers of electrodes can be used, then larger areas can be stimulated to produce more effective pain relief. However, increased stimulation area cannot be achieved by simply increasing electrode size since most of the energy flows between the closest points of approach of the electrodes. In addition, increasing excitation between electrodes will increase the current density through the skin. Furthermore, electrodes may inadvertently touch each other or be fired simultaneously or be superimposed on each other. These conditions may result in a sensation which may be more painful than the pain to be alleviated.

Hence, current instruments do not lend themselves to simple modification to accomplish the main objects of this invention, i.e. increasing the stimulation area without danger of injury to the patient and providing a form of stimulation which permits rather than forces the tissue to accept energy. Some of them deliver pulses of adjustable constant current at variable repetition rates. Others have adjustable compliance and some are capable of supplying the electrodes either simultaneously or alternately. Still others supply unipolar excitation while some supply bipolar ones. Not all of the current instruments are constant current types. Some are high impedance pulse generators, others modulate the peaks of the pulses while still other do not. There appears to be as many waveforms as there are manufacturers with no consensus as to what is the best.

An important object of the present invention is to provide a dissipative, extremely low cost, transformerless battery charger suitable for incorporation into a host of small electrical devices, such as electrical shavers, lawn tools, radios, and the like, in addition to the transcutaneous pain reliever forming the subject matter of the parent application and patent identified above. As will be explained in greater detail below, the invention provides an extremely simple and low cost circuit of the character described to thereby constitute a substantial step forward in the battery charger arts.

Thus, a purpose of the invention is to provide a charger of the character described wherein there is no transformer, thus saving the weight of a transformer. In addition, the invention uses low-cost, low-voltage diodes. In addition, the invention provides current limiting means, capacitors or resistors for example, in series with the diode bridge, and not in series with the batteries. A zener diode is provided on the side of the bridge between the diode bridge and the batteries. Thus, a low surely nonlethal voltage is at all times provided across the battery terminal connections of the charger, even when the battery is not in place being charged. This low harmless voltage is present in place of a higher potentially dangerous voltage, regardless of the magnitude of the supply voltage which may be used at the opposite side, opposite the zener diode, of the diode bridge.

Another object of the present invention is the provision of an improved battery charger in which a transformerless, bridged battery charger circuit is used to permit inexpensive low power voltage signal diodes to be used regardless of the magnitude of a much higher charging voltage source.

Another object of the present invention is the provision of an improved device and circuit in which the battery charger is automatically mechanically disconnected from the main patient connectable circuitry when it is charging.

Another object of the present invention is the provision of an improved device and circuit in which a battery saver is provided as an option so that excess energy not delivered to electrodes can be returned to the batteries.

Other and further objects of the invention will be obvious upon an understanding of the illustrative embodiment about to be described, or will be indicated in the appended claims, and various advantages not referred to herein will occur to one skilled in the art upon employment of the invention in practice.

A preferred embodiment of the invention has been chosen for purposes of illustration and description and is shown in the accompanying drawings forming a part of the specification, wherein the sole FIG. 1 is a schematic view showing the circuitry of the battery charger, the clocking system and the antiadapt system used in accordance with the present invention.

The battery charger of the present invention is shown schematically in FIG. 1. The power for the instrument is obtained from a plurality or chain of batteries B1 to B4. A switch S3 controls the battery chain connections between CHARGE, OFF and ON.

The invention battery charger is shown in the lower left hand corner of FIG. 1, the circuitry to the right is the batteries being charged. The remaining circuitry in the upper part of FIG. 1 comprises part of the transcutaneous pain reliever circuit described more in detail in the aforementioned prior patent and prior application to which this application is related. That subject matter has been incorporated herein by reference, and thus need not be described in further detail at this point.

The charger unit is a bridged, transformerless bridge rectifier unit which permits the use of low voltage inexpensive diodes (such as 25 V PIV,) on a 230 volt line. The battery charger comprises diodes D3, D4, D5 and D6 which are arranged as a bridge. A zener diode D8 is used across the output of the bridge. Zener diode D8 permits the batteries B1 to B4 to be disconnected from the bridge without subjecting the bridge diodes to large inverse voltages. The voltage limiting zener D8 is no larger than the breakdown voltage of zener D8 so that the zener diode D8 protects the low voltage bridge diodes D3 to D6 when the battery is disconnected from the charger and the charging circuit is still receiving power from the main power line.

Since the voltage of zener D8 is greater than the battery voltage, the zener D8 has no effect when the batteries B1–B4 are connected to the charger by switch S3. However, if the batteries B1–B4 are disconnected from the charger, the zener D8 absorbs the charging current while insuring that the maximum voltage across the bridge diodes D3–D6 is only slightly greater than it would have been with the batteries in place. Thus, even though the charging voltage supply is very high, the bridge diodes D3–D6 require a rating only slightly greater than that of the zener diode voltage of D8 which in turn is only slightly greater than the battery voltage.

The voltage of the zener diode D8 depends upon the battery requirements and, in the example illustrated, is preferably between 10 and 15 volts. The batteries B1–B4 are 150 milliampere-hour batteries which may be recharged at 15 milliamperes. Preferably, they are nickel cadmium batteries of about 1.41 volts approximately, so that the battery chain total is 5.64 volts at end of charge. Suitable batteries which have been used have a nominal discharge characteristic of about 10% of capacity between 1.41 and 1.25 volts, 80% of capacity between 1.25 and 1.1 volts, and 10% thereafter. The LED D9 requires about 1.6 volts and the reverse voltage protection diode D7 requires about 0.7 volts. Hence, breakdown voltage of zener diode D8 is such that no current passes through it when the battery assembly B1–B4 is connected to the bridge D3–D6 by switch S3 being in the CHARGE position. Under such circumstances, the voltage from D7 to the cathode of zener D8 is approximately 8 volts so that if D8 is of greater voltage, e.g. about 10 volts, no current passes.

When the switch S3 is not in the CHARGE position but in the OFF or the ON positions, the output of the bridge D3–D6 is absorbed by zener diode D8. The current is limited by the resistors R15 and R16 to about 15 milliamperes under either 230 volt or the 115 volt depending upon the position of switch S4, some contacts of which are not used as a switch but rather as a set of points on which to mount the resistor R16. The inclusion of zener D8 across the bridge D3–D6 with the accompanying voltage dropping resistors prevents the diodes in bridge D3–D6 from being subjected to any voltage greater than the breakdown voltage of the zener diode D8 in all positions of battery switch S3.

As described above, the resistors R15 and R16 serve a current limiting function. Other means to limit the current such as inductors or capacitors for example, could be used, and thus the critical part of the invention is the provision of some sort of current limiting means, rather than resistors specifically, between the diode bridge and the supply voltage.

The diode D7 reinforces the reverse impedance of the LED D9, and thereby prevents the batteries from discharging themselves if the line source is disconnected from the network while the selector switch S3 is inadvertently left in the charging, left side, position. This battery saving feature is, again, provided by the very simple array of low cost parts, namely the diode D7 and the LED D9 arranged in a simple circuit as shown.

D9 is primarily a charge-in-process indicator. Where indication is not required, and the conductance combination is negligeable, both D7 and D9 may be deleted. Where indication is required and the combined conductance of the bridge and zener is negligeable, D7 may be deleted, although it is less expensive to include it and not pay the premium required to guarantee the low conductance of the bridge-zener combination.

The energy generator chassis circuitry shown and described in complete detail in the above identified predecessor patent and application incorporated herein by reference, is incorporated in a circuit separate from the control chassis containing the batteries so that the physical interconnection of the two circuits makes it impossible to recharge the batteries while they are connected to the energy chassis. Hence, there can be no physical connection between the main power line and the person undergoing treatment while the batteries are being charged since the batteries must be separated from the control chassis before they are charged.

Thus, in summary, the invention provides a diode bridge of the diodes D3, D4, D5 and D6, arranged between current limiting means, such as capacitors or the resistors R15 and R16 on the supply side, and the zener diode D8 on the battery side. The voltages of these three elements of the invention battery charger are selected such that the current limiting means reduces the current to a low enough value that low cost elements can be used in the diode bridge, and the value of the voltage of this bridge is selected to be slightly more than the value of the protective zener diode D8. In this manner, the user is protected against potentially harmful and even fatal shocks which could otherwise be present were he exposed to the relatively high voltage used on the input side of the current limiting means; 230 volts AC in the preferred embodiment. Further, the simple series array of the protective diode D7 and the LED D9 prevents leakage of the batteries in the event the charger switch leaves the batteries connected to the circuit and the power source is disconnected. Absent this protective feature, the batteries could self-discharge by leaking back through the charger circuit.

While the invention has been described in detail above, it is to be understood that this detailed description is by way of example only, and the protection granted is to be limited only within the spirit of the invention and the scope of the following claims.

I claim:

1. A transformerless battery charger comprising a bridge assembly having a plurality of diodes arranged in a bridge, said bridge assembly having means to permit batteries to be charged to be connected thereto, a zener diode assembly across the output of said bridge assembly, means connecting the bridge assembly to a charging voltage source, means to limit the flow of current from said charging voltage source into said bridge assembly, said zener diode assembly breakdown voltage being greater than the battery voltage, and the bridge diode assembly voltage rating being greater than the zener diode breakdown voltage; said current limiting means between said source and said bridge and said voltage relationships between said bridge, said zener diode and said batteries being such as to permit direct use of relatively large voltages at said source without the intervention of a transformer while using diodes in said bridge of relatively low ratings and of relatively low cost; and said battery charger being so arranged that the output of said diode bridge is absorbed by said zener diode when said batteries to be charged are disconnected from said diode bridge.

2. A battery charger as claimed in claim 1, and switch means for selectively connecting said diode bridge to said batteries which are to be charged.

3. A battery charger as claimed in claim 2 and switch means to connect said batteries to an extended electrode.

4. A battery charger as claimed in claim 3, wherein the same switch means are used so that connections of the batteries to said electrical source automatically disconnects the batteries from said bridge, or wherein connection of batteries to the diode bridge assembly automatically disconnects the batteries from the external electrodes.

5. A battery charger as claimed in claim 1, and an LED in series circuit with said diode bridge between said diode bridge and said means to permit said batteries to be charged.

6. A battery charger as claimed in claim 5 and a reverse voltage protective diode in series circuit with said LED.

7. A battery charger as claimed in claim 1, wherein said current limiting means comprises resistor means of predetermined value.

8. A battery charger as claimed in claim 1, wherein said current limiting means comprises capacitor means of selected values for determining one of said different charging voltages.

9. A battery charger as claimed in claim 1, wherein said charging voltage source is on the order of 230 volts AC, said current limiting means limit the voltage to about 12 volts, said diode bridge being rated at about 12 volts, said zener diode breakdown voltage being about 10 volts, and the voltage of the batteries to be charged being about 5.6 volts.

10. A battery charger as claimed in claim 1, wherein said current limiting means are connected to said diode bridge, and switch means associated with said current limiting means to permit different charging voltages to be connected to said diode bridge while limiting the current from said source into said diode bridge at all of said different charging voltages.

11. A battery charger as claimed in claim 1, wherein said batteries to be charged are part of a portable instrument.

12. A battery charger as claimed in claim 11, wherein each battery of the batteries to be charged is of 150 ma-hr capacity.

* * * * *